United States Patent
Sasaki (12)

(10) Patent No.: US 6,977,784 B2
(45) Date of Patent: Dec. 20, 2005

(54) IMAGE-TAKING APPARATUS

(75) Inventor: Hidenori Sasaki, Ayase (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 10/401,705

(22) Filed: Mar. 31, 2003

(65) Prior Publication Data

US 2003/0184853 A1    Oct. 2, 2003

(30) Foreign Application Priority Data

Mar. 29, 2002  (JP) .............................. 2002-094804

(51) Int. Cl.[7] .............................. G02B 5/22; G02B 7/04
(52) U.S. Cl. ...................... 359/892; 359/379; 396/144
(58) Field of Search ................................ 359/892, 889, 359/891, 707, 890, 391, 823, 824, 888, 379, 359/392, 822; 396/144, 349, 422; 356/300

(56) References Cited

U.S. PATENT DOCUMENTS 3,813,167 A * 5/1974 Johnson et al. ............. 356/300
4,013,347 A * 3/1977 Nakamura ................... 359/707
5,987,262 A * 11/1999 Higuchi et al. ............. 396/144

* cited by examiner

*Primary Examiner*—Audrey Chang
(74) *Attorney, Agent, or Firm*—Sughrue Mion, PLLC (57) ABSTRACT

An image-taking apparatus includes an image-taking portion provided with a taking lens system. A filter to be brought into close contact with the taking lens system is held by a filter holder. A moving mechanism moves a movable member in the direction of the optical axis of the taking lens system. A spring intervenes between the filter holder and the movable member and urges the filter holder toward the taking lens system in the direction of the optical axis thereof.

14 Claims, 7 Drawing Sheets

IMAGE-TAKING APPARATUS

BACKGROUND OF THE INVENTION

1. Field of the Invention

This invention relates to an image-taking apparatus, and more particularly to an image-taking apparatus having a filter in contact with a lens system.

2. Description of the Related Art

There has been known an image-taking apparatus which images weak fluorescence emitted from a sample in a dark box. A plurality of filters different in transmission properties are prepared for the taking lens employed in such an image-taking apparatus and one of the filters is mounted on the taking lens according to the kind of the sample to be photographed.

There has been a demand for automatically mounting a filter on the taking lens and an electric filter changing system has been investigated. In order to bring a filter in close contact with a taking lens by electric control, change of the total length of the taking lens caused by focusing must be taken into account. That is, when the filter to be positioned in front of the taking lens is held away from the taking lens due to focusing, the filter can obstruct the field of view of the taking lens, or light traveling through the gap between the taking lens and the filter can cause noise. Accordingly, the filter changing system must be provided with a function to move the selected filter following extension and contraction of the taking lens with the filter held in close contact with the front end of the taking lens.

However, in order to move the filter following extension and contraction of the taking lens with the filter held in close contact with the front end of the taking lens, control to move the filter in the direction of the optical axis of the taking lens while detecting the position of the front end of the taking lens is necessary, and especially when one of a plurality of taking lenses is selected as the taking lens, the difference in the total length of the taking lens more complicates the control, which results in high cost.

SUMMARY OF THE INVENTION

In view of the foregoing observations and description, the primary object of the present invention is to provide an image-taking apparatus which is simple in the mechanism of bringing the filter into close contact with the taking lens and accordingly can be manufactured at low cost.

In accordance with the present invention, there is provided an image-taking apparatus comprising an image-taking means provided with a taking lens system, a filter holder means which holds a filter to be brought into close contact with the taking lens system, a movable member, a moving means which moves the movable member in the direction of the optical axis of the taking lens system, and an urging means which intervenes between the filter holder means and the movable member and urges the filter holder means toward the taking lens system in the direction of the optical axis thereof.

The filter holder means may comprise, for instance, a holding portion which holds a plurality of filters, and a support portion which movably supports the holding portion so that each of the filters held by the holding portion can be positioned on the optical axis of the taking lens system.

The image-taking apparatus of the present invention may further comprise a linkage which links the filter holder means with the movable member so that the filter holder means is moved away from the taking lens system in response to movement of the movable member away from the taking lens system.

The urging means urges the filter holder means toward the taking lens system in the direction of the optical axis thereof and causes the filter holder means to follow the movement of the taking lens system with the filter held in close contact with the taking lens system. For example, the urging means urges the filter holder means to follow the movement of the front end of the taking lens system during focusing constantly pressed against the front end of the taking lens system at a substantially constant pressure. As such an urging means, a resilient urging means such as a spring may be employed.

In the image-taking apparatus of the present invention, by virtue of the urging means which intervenes between the filter holder means and the movable member and urges the filter holder means toward the taking lens system in the direction of the optical axis thereof, the filter holder means can be moved following the change of the position of the front end of the taking lens system due to focusing to hold the filter in close contact with the front end of the taking lens system, whereby the mechanism of bringing the filter into close contact with the taking lens is simplified and accordingly, the image-taking apparatus can be manufactured at low cost.

Further, when the filter holder means comprises a holding portion which holds a plurality of filters, and a support portion which movably supports the holding portion so that each of the filters held by the holding portion can be positioned on the optical axis of the taking lens system, the filter can be quickly changed.

Further when the image-taking apparatus of the present invention further comprises a linkage which links the filter holder means with the movable member so that the filter holder means is moved away from the taking lens system in response to movement of the movable member away from the taking lens system, the filter is prevented from being unnecessarily held in close contact with the taking lens system urged by the urging means when the filter holder means is moved away from the taking lens system, whereby, for instance, change of the taking lens system can be quickly done.

DESCRIPTION OF THE PREFERRED EMBODIMENT

Figure 1:
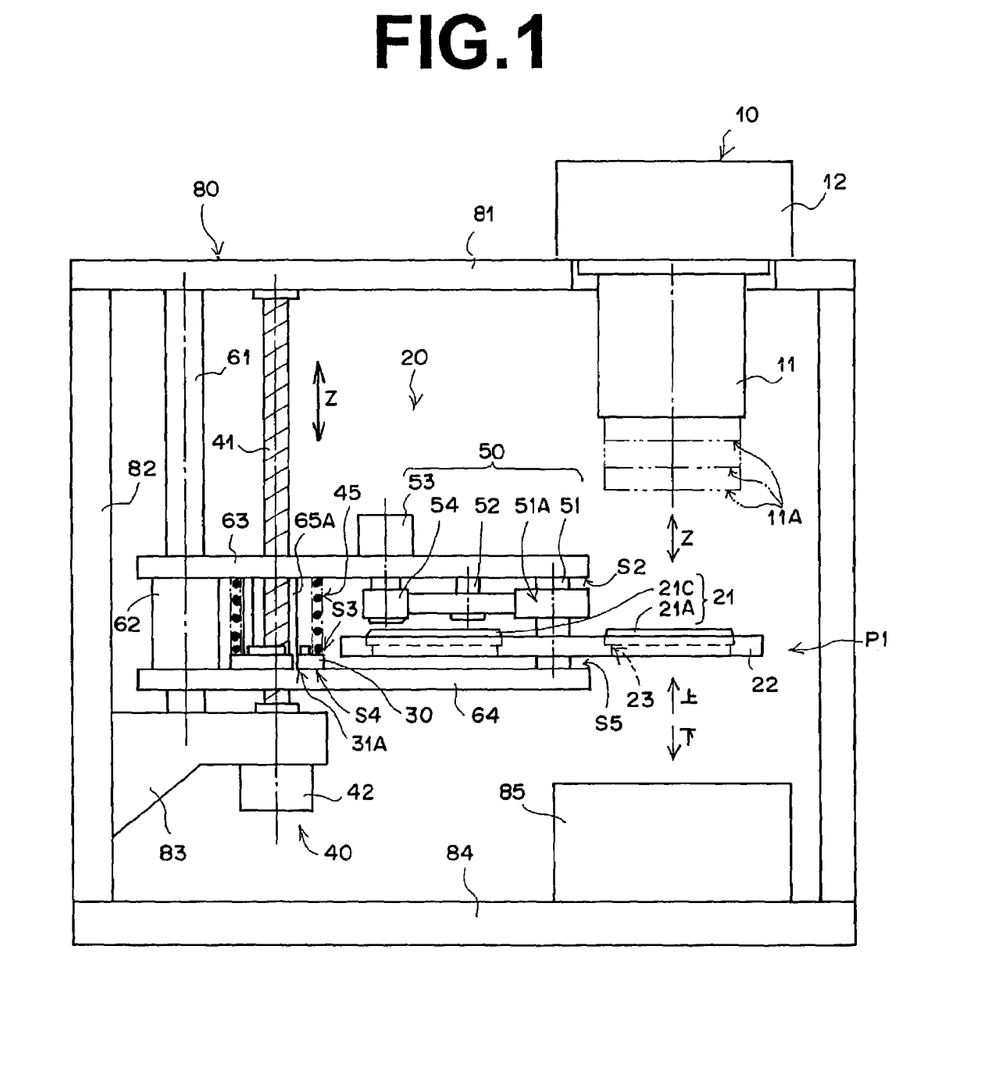
FIG. 1 is a side view showing in brief an image-taking apparatus in accordance with an embodiment of the present invention.

In FIG. 1, an image-taking apparatus in accordance with an embodiment of the present invention comprises an image-taking means 10 provided with an interchangeable lens 11, a filter holder means 20 which holds a filter 21 to be brought into close contact with the interchangeable lens 11, a movable nut 30, a nut moving means 40 which moves the movable nut 30 in the direction of the optical axis of the interchangeable lens 11 (in the direction of arrow Z, will be referred to simply as "in the direction of the optical axis Z", hereinbelow), and a coiled spring 45 which intervenes between the filter holder means 20 and the movable nut 30 and urges the filter holder means 20 toward the interchangeable lens 11 in the direction of the optical axis Z.

Figure 2:
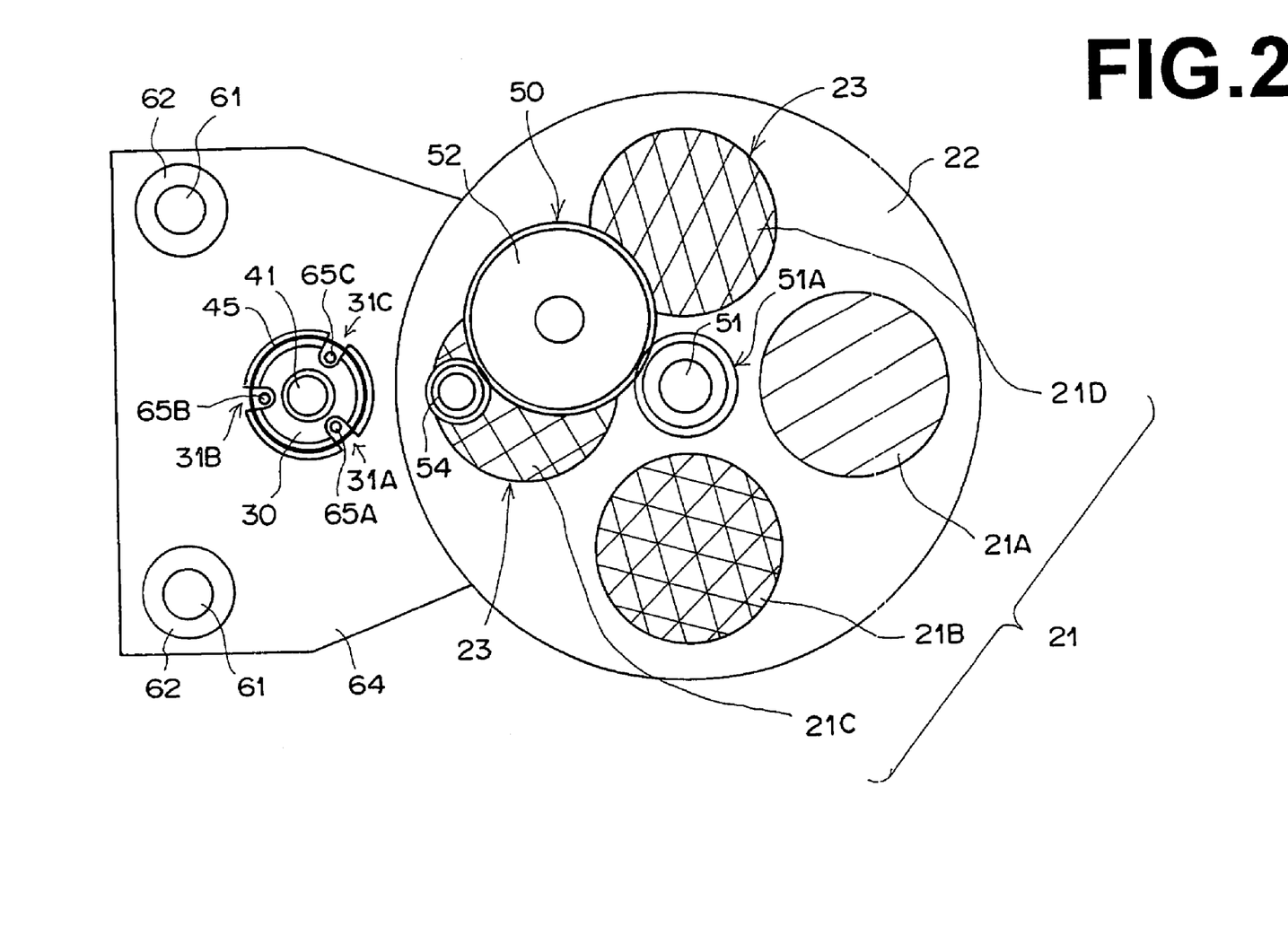
FIG. 2 is a plan view showing in brief the filter holder means and the nut moving means.

The filter holder means 20 comprises a holding portion 22 (FIG. 2) having a plurality of (four in this particular embodiment) filter holding openings 23 for holding filters 21A, 21B, 21C and 21D, and a filter rotating portion 50 which supports the holding portion 22 to be rotatable to bring each of the filters 21A, 21B, 21C and 21D held by the holding portion 23 on the optical axis Z of the interchangeable lens 11.

The image-taking apparatus of this embodiment further comprise a bottom plate 64 which links the filter holder means 20 with the movable not 30 so that the filter holder means 20 is moved away from the interchangeable lens 11 in response to movement of the movable nut 30 away from the interchangeable lens 11. The bottom plate 64 also forms a part of the filter holder means 20.

The interchangeable lens 11, the filter holder means 20, the movable nut 30, the nut moving means 40 and the coiled spring 45 are accommodated in a dark box 80.

The image taking means 10 comprises, in addition to the interchangeable lens 11, an image taking portion 12 supported by a top plate 81 of the dark box 80. The interchangeable lens 11 has an autofocus mechanism, and the amount by which the front end portion 11A is fed forward is automatically adjusted according to the distance to an object placed in a sample table 85 on a bottom plate 84 of the dark box 80.

The filter holder means 20 is further provided with a pair of cylindrical shafts 61 extending in parallel to the optical axis Z between the top plate 81 of the dark box 80 and an intermediate plate 83 which is mounted on a side plate 82 to extend in parallel to the surface of the top plate 81, a ball bushing 62 which is fitted on each of the shafts 61 to be movable along the shaft 61, and upper and lower plates 63 and 64 respectively provided on the upper and lower sides of the bushing 62. The shafts 61 and the ball bushings 62 for a so-called linear slide and the upper and lower plates 63 and 64 are movable along the shafts 61 in the direction of optical axis Z by virtue of the linear slide.

The filter rotating portion 50 comprises a pivot shaft 51 which is connected to the holding portion 22 by way of the center of the surface of the holding portion 22 on which the filters 21 (21A, 21B, 21C and 21D) are supported and is connected for rotation to the upper and lower plates 63 and 64 at its opposite ends, an intermediate gear 52 which is supported for rotation by the upper plate 53 and is in mesh with gear teeth 61A on the pivot shaft 51, and a stepping motor 53 which is provided on its output shaft with gear teeth 54 in mesh with the intermediate gear 52. The holding portion 22 is rotated by the stepping motor 53 by way of the gear teeth 54, the intermediate gear 52 and the pivot shaft 51. As the holding portion 22 is rotated, the filters 21A, 21B, 21C and 21D are brought on the optical axis Z in sequence.

The nut moving means 40 comprises a ball screw 41 which is supported for rotation by the top plate 81 and the intermediate plate 83 at its upper and low ends and in mesh with the movable nut 30, and a stepping motor 42 which is disposed on the side of the intermediate plate 83 remote from the ball screw 41 with its output shaft extending through the intermediate plate 83 and connected to the ball screw 41. As the stepping motor 42 rotates, the ball screw is rotated and the movable nut 30 in mesh with the ball screw 41 is moved in the direction of the optical axis Z.

Three stopper pins 65A, 65B and 65C extend through cutaway portions 31A, 31B and 31C formed in the outer periphery of the movable nut 39 and are connected for rotation to the upper and lower plates 63 and 64 at upper and lower ends thereof. The stopper pins 65A, 65B and 65C prevents the movable nut 30 from being rotated about the ball screw 41 so that the movable nut 30 is moved in the direction of the optical axis Z upon rotation of the stepping motor 42.

The coiled spring 45 intervenes between the lower surface S2 of the upper plate 63 of the filter holder means 22 and the upper surface S3 of the movable nut 30, and urges the upper plate 63 toward the interchangeable lens 11, thereby urging the overall filter holder means 20 in the direction of the optical axis Z.

The stepping motors 53 and 42 are controlled by a controller not shown.

Operation of the image-taking apparatus of this embodiment will be described, hereinbelow.

That is, the stepping motor 42 is rotated to move the movable nut 30 away from the image-taking means 10 in the direction of the optical axis Z, and press downward the upper surface S5 of the lower plate 64 by the lower surface S4 of the movable nut 30, whereby the filter holder means 20 is moved downward away from the image-taking means 10 along the shafts 61 to stand-by position P1.

When the stepping motor 42 is rotated in the regular direction, the movable nut 30 is moved toward the image-taking means 10 in the direction of the optical axis Z whereas when the stepping motor 42 is rotated in the reverse direction, the movable nut 30 is moved away from the image-taking means 10 in the direction of the optical axis Z.

Then a selected one of interchangeable lenses 11 is manually mounted on the image-taking portion 12.

Subsequently, the stepping motor 53 is driven to rotate the holding portion 22 to bring one of the filters 21A to 21D on the optical axis X (it is assumed here that the filter 21A is selected for the purpose of simplicity).

Then the stepping motor 42 is rotated in the regular direction to move the movable nut 30 toward the image-taking means 10, thereby moving the upper plate 63 upward with the upper plate 63 kept urged by the coiled spring 45 and moving the filter holder means 20 toward the image-taking means 10.

Figure 3:
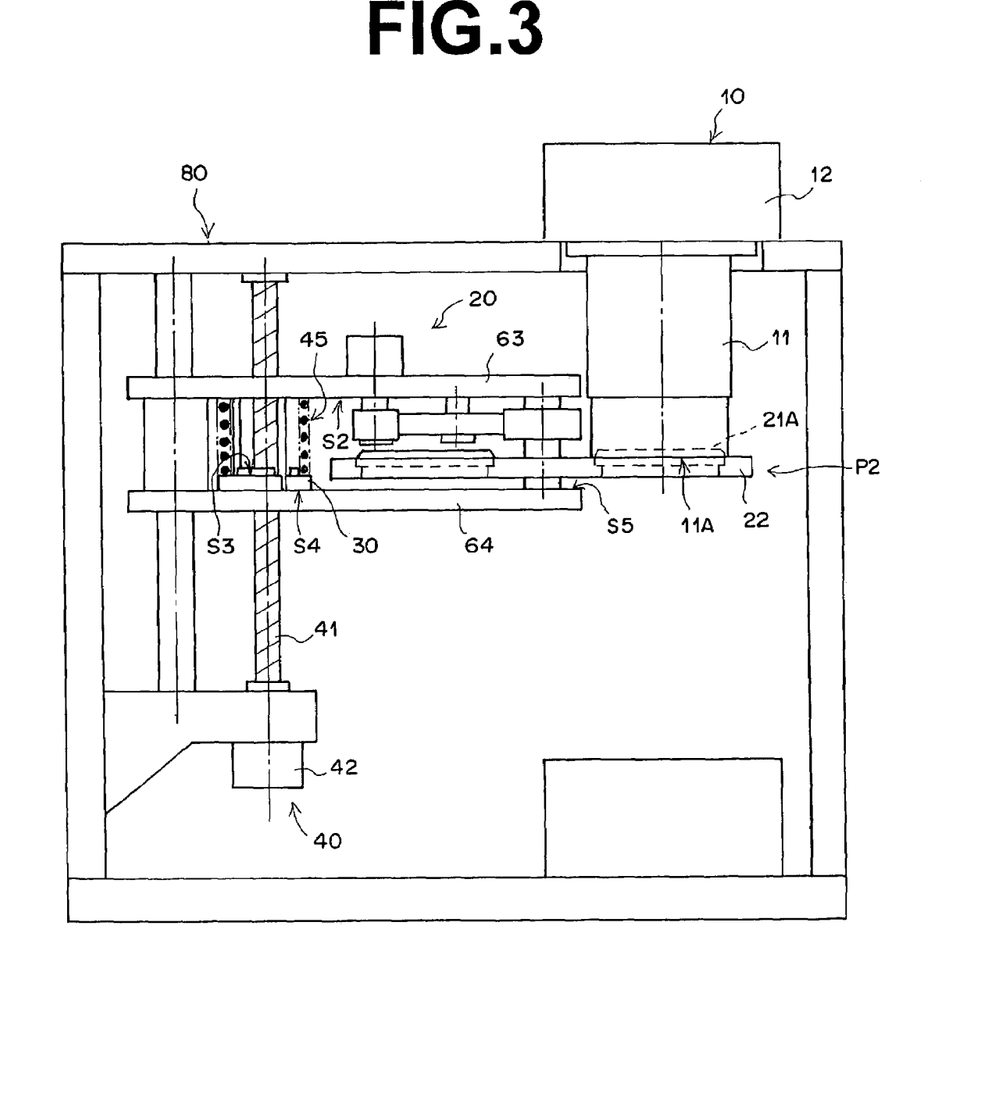
FIG. 3 is a side view showing a state where the filter is brought into contact with an interchangeable lens.

When the filter holder means 20 is moved upward toward the image-taking means 10 in the direction of the optical axis Z, the outer frame of the filter 21A is brought into contact with the front end 11A of the interchangeable lens 11 in position P2 as shown in FIG. 3. Further rotation of the stepping motor 42 in the regular direction cannot not move further upward the filter 21A and the filter 21A is held stationary in position P2. Accordingly, the filter rotating portion 50 and the filter holder means 20 are also held stationary there.

Whereas, further rotation of the stepping motor 42 moves upward the movable nut 30 in the direction of the optical axis Z away from the upper surface S5 of the lower plate 64, whereby the coiled spring 45 between the upper surface S3 of the movable not 30 and the lower surface S2 of the upper plate 63 which is held stationary is compressed. That is, the filter holder means 20 presses the filter 21A against the interchangeable lens 11 into close contact therewith under the force of the coiled spring 45.

Figure 4:
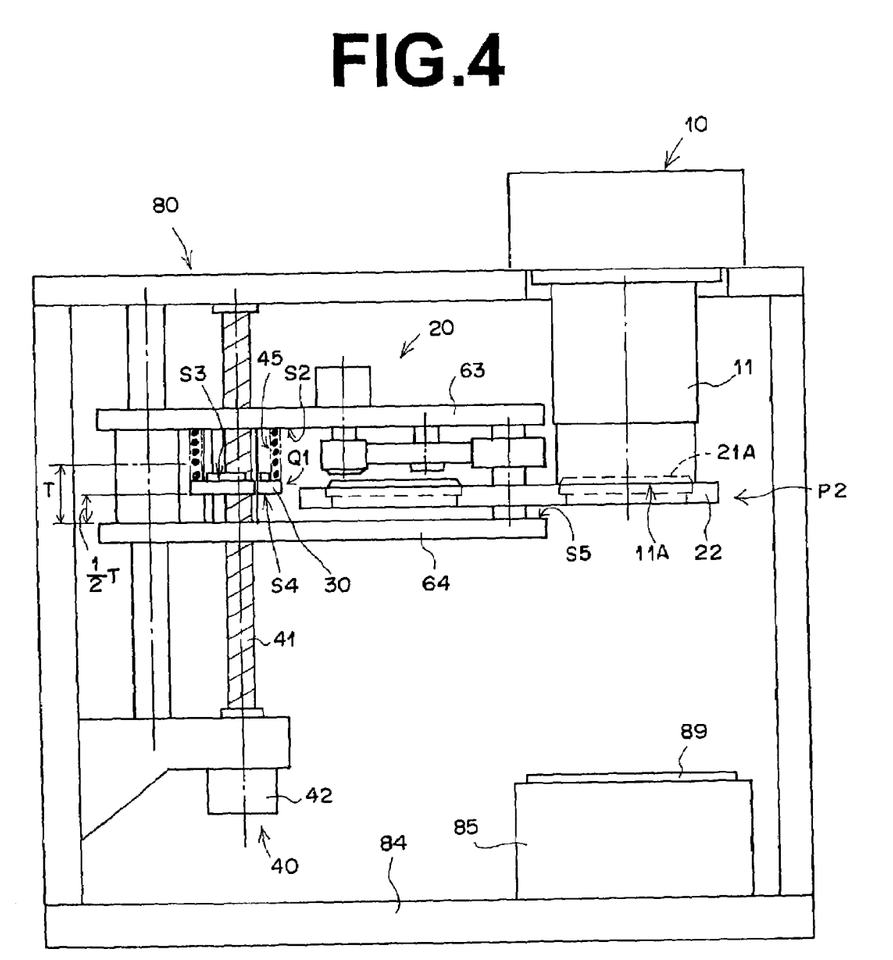
FIG. 4 is a side view showing a state where the filter urges the interchangeable lens.
Figure 5:
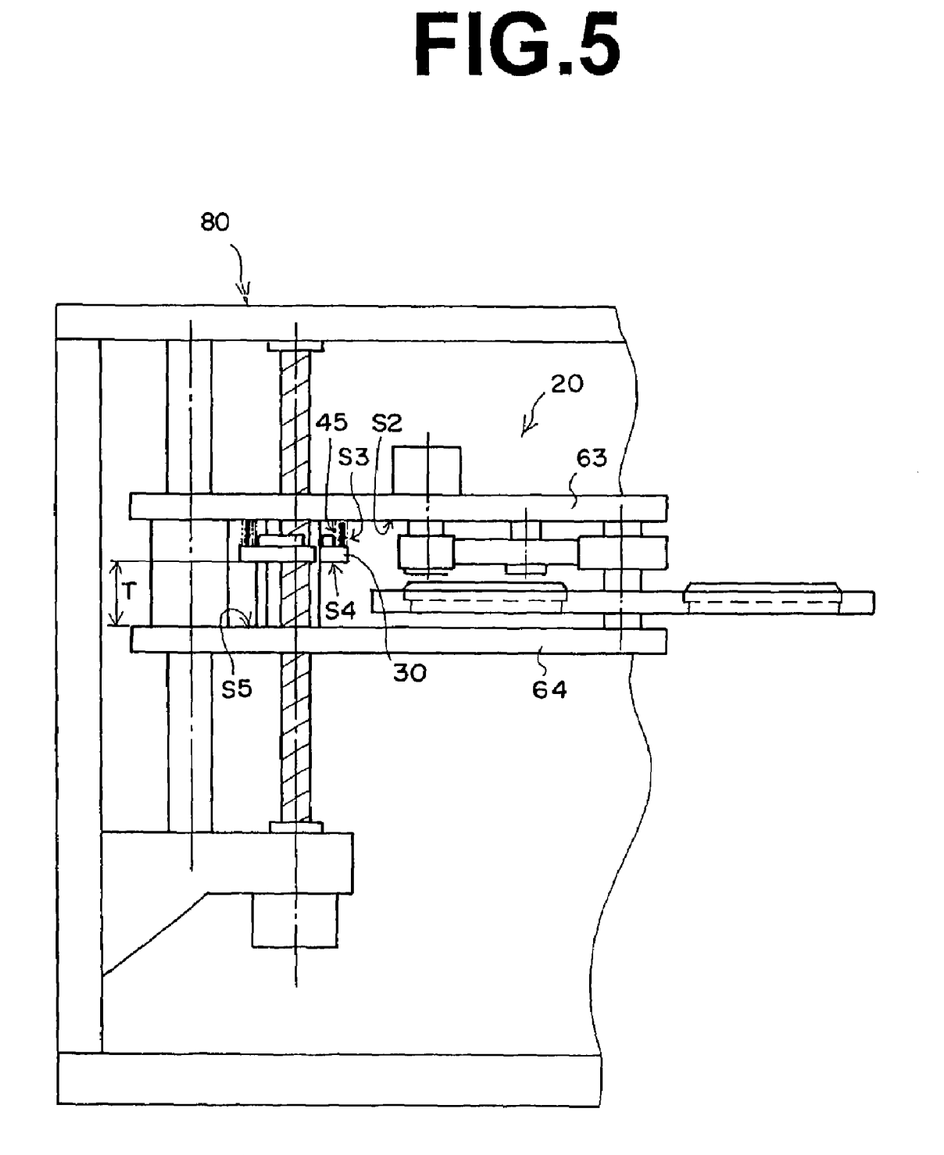
FIG. 5 is a view showing the maximum stroke T of the movable nut.

When the movable nut 30 is brought to position Q1 (FIG. 4) where the amount of movement of the movable nut 30 is about half of the maximum stroke T of the movable nut 30, that is, the number of drive pulses reaches a value corresponding to the distance about half of the maximum stroke T of the movable nut 30, the stepping motor 42 is stopped. The maximum stroke T of the movable nut 30 is defined as the distance between the lower surface S4 of the movable nut 30 and the upper surface S5 of the lower plate 64 when the coiled spring 45 is compressed to the limit with the distance between the upper surface S3 of the movable nut 30 and the lower surface S2 of the upper plate 63 minimized. (see FIG. 5)

Thereafter, a sample 89 is placed on the sample table 85 in the dark box 80 and the autofocus mechanism of the interchangeable lens 11 is operated, whereby the interchangeable lens 11 is automatically focused so that an image of the sample 89 is accurately focused on the image-taking plane of the image-taking portion 12. In response to operation of the autofocus mechanism, the position of the front end portion 11A of the interchangeable lens 11 is changed.

Figure 6:
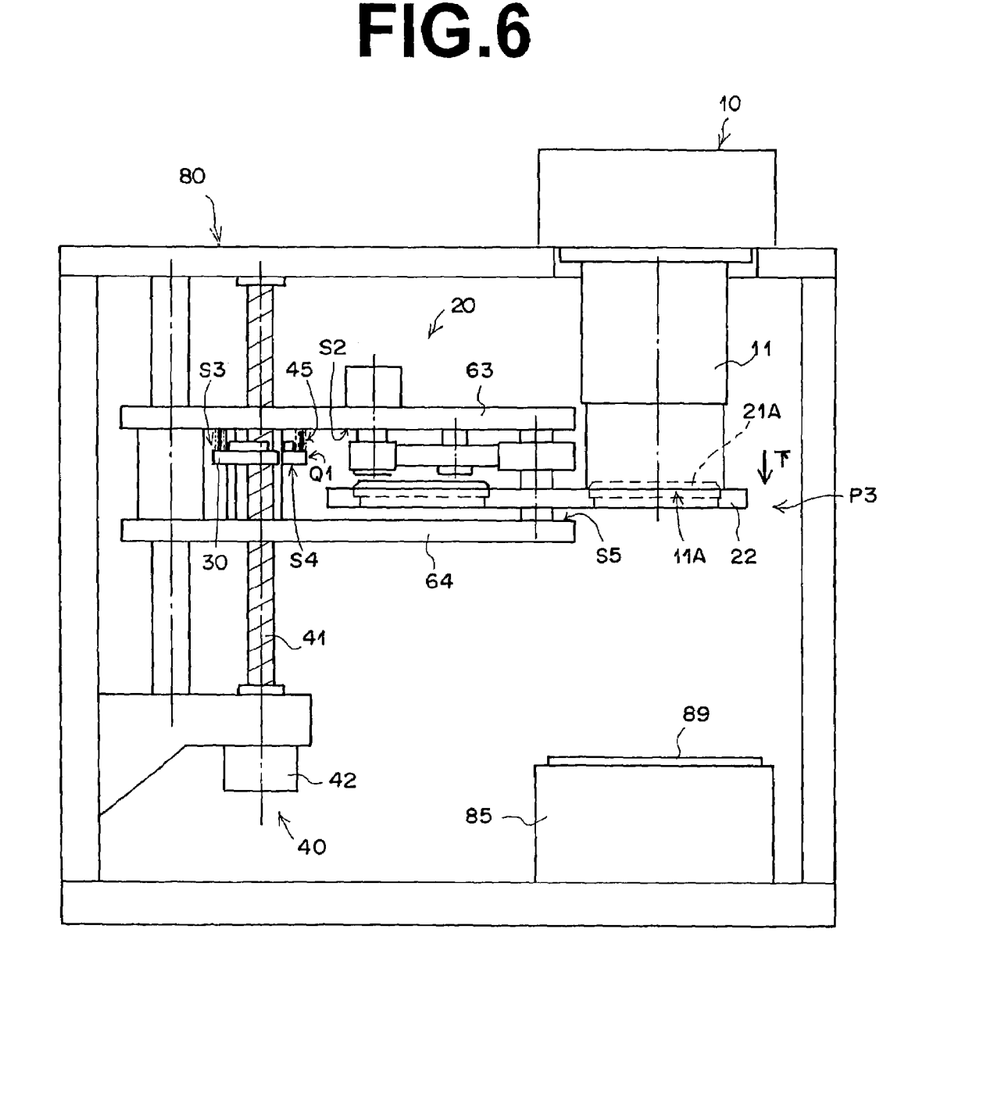
FIG. 6 is a side view showing the image-taking apparatus in a state where the front end portion of the interchangeable lens with the filter held in close contact therewith is in a forward position.

The filter 21A urged toward the end portion 11A of the interchangeable lens 11 by the coiled spring 45 follows the front end portion 11A of the interchangeable lens 11 held in close contact therewith. That is, when the amount by which the front end portion 11A of the interchangeable lens 11 is fed forward (downward) is increased and the front end portion 11A is moved to position P3, the upper plate 63 is moved downward together with the filter 21A and the distance between the lower surface S2 of the upper plate 63 and the upper surface S3 of the movable nut 30 is reduced, whereby the coiled spring 45 is further compressed. (FIG. 6) At this time, the movable nut 30 is held stationary in the position Q1.

Figure 7:
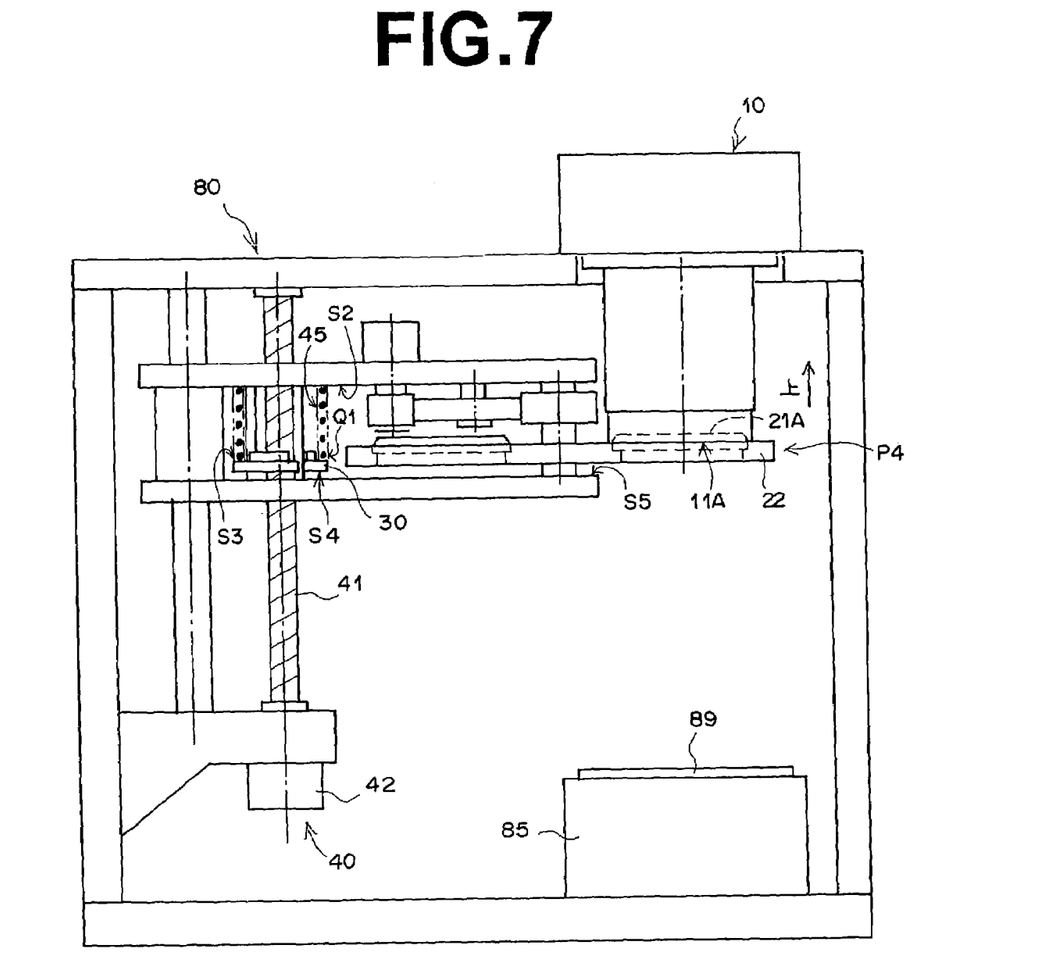
FIG. 7 is a side view showing the image-taking apparatus in a state where the front end portion of the interchangeable lens with the filter held in close contact therewith is in an original position.

When the amount by which the front end portion 11A of the interchangeable lens 11 is fed forward is decreased and the front end portion 11A is moved to position P4 as shown in FIG. 7, the upper plate 63 is moved upward under the force of the coiled spring 45 and the distance between the lower surface S2 of the upper plate 63 and the upper surface S3 of the movable nut 30 is increased, whereby the coiled spring 45 comes to be less compressed. Also at this time, the movable nut 30 is held stationary in the position Q1.

As can be understood from the description above, in the image-taking apparatus of this embodiment, by only once adjusting the position of the movable nut 30 to the position Q1, the filter 21A can be held in close contact with the interchangeable lens 11 under the urging force of the coiled spring 45 even if the position of the front end portion 11A of the interchangeable lens 11 varies due to focusing action.

Accordingly, even when the position of the front end portion 11A of the interchangeable lens 11 is changed due to autofocusing action caused when the position of the object in the direction of the optical axis Z changes, the filter 21A can be held in close contact with the interchangeable lens 11 so long as the movable nut 30 is in position Q1.

When the filter is changed, the stepping motor 42 is rotated in the reverse direction to move downward the movable nut 30 to a position in which the filter 21A is away from the interchangeable lens 11, and then the filter is changed by operating the filter rotating portion 50. Thereafter, the stepping motor 42 is rotated in the regular direction to return the movable nut 30.

The movable nut 30 can be returned to the position Q1 by remembering the number of drive pulses.

By employing double gears in the driving force transmission mechanism of the filter rotating portion 50 to suppress backlash of the gears, filter positioning accuracy can be improved.

Though, in the embodiment described above, a coiled spring is employed as the urging means, any other suitable means such as a leaf spring, an air cylinder or an electromagnet may be employed as the urging means. Further, the moving means need not comprise a ball screw and a movable nut but may be of any system so long as it can move the movable member to a desired position in the direction of the optical axis Z.

Further the support portion need not be limited to those which automatically moves the holding portion but may be arranged to manually move the holding portion.

Further, the number of filters held by the filter holder means need not be limited to four.

Further, the image-taking apparatus of the present invention need not be provided with a linkage, but without a linkage, the mechanism of bringing the filter into close contact with the taking lens can be simplified.

The image-taking apparatus of the embodiment described above is characterized in that the filter is held in close contact with the taking lens by pressing the filter against the taking lens. Accordingly, when the force of the coiled spring is too strong, the taking lens can be defocused with the lapse of time under the force of the coiled spring depending on the lens feeding mechanism. In order to avoid this problem, and in order to deal with a larger change of the position of the front end of the taking lens, it is necessary to design the image-taking apparatus with the strength of coiled spring confined within a predetermined range. That is, it is necessary to confine the strength of coiled spring so that it is sufficient to support the weight of the filter holder means but insufficient to push back the movable part of the taking lens.

Thus, design of the urging means (including the coiled spring) requires a special consideration.

An example of design of the coiled spring will be described, hereinbelow.

In the case where the taking lens is such that the front end is fed forward by 40 mm at the maximum and the coiled spring is to be able to deal with the amount of feed, the coiled spring is designed as follows.

spring rate: 0.05 to 0.15 N/mm
length in a free state: 150 to 200 mm
working range: a range in which the coiled spring is compressed to 10 mm to 50 mm.

When a coiled spring which 0.1 N/mm in spring rate and 180 mm in length in a free state is employed in the above setting, the force of the coiled spring changes in the range of about 13 N to 17 N (this force will be referred to as "A", later).

On the other hand, the coiled spring supports also the filters and the filter holder means (sometimes referred to as a filter changing mechanism or a filter changer unit). Since load on the coiled spring changes in response to, for instance, demounting a filter from the filter holder means, the force B required for the coiled spring to support the filters and the filter holder means changes within the range of 9 N to 12 N.

In total, the force of the coiled spring to push back the movable part of the taking lens is (A)–(B), which changes within the range of 1 N to 8 N. That is, the urging force, or the force of the coiled spring to push back the movable part of the taking lens, is 8 N at the maximum, and accordingly, a taking lens system which can withstand this force should be employed.

What is claimed is:

1. An image-taking apparatus comprising an image-taking means provided with a taking lens system, a filter holder means which holds a filter to be brought into close contact with the taking lens system, a movable member, a moving means which moves the movable member in the direction of the optical axis of the taking lens system, and an urging means which intervenes between the filter holder means and the movable member and urges the filter holder means toward the taking lens system in the direction of the optical axis thereof.

2. An image-taking apparatus as defined in claim 1 in which the filter holder means comprises a holding portion which holds a plurality of filters, and a support portion which movably supports the holding portion so that each of the filters held by the holding portion can be positioned on the optical axis of the taking lens system.

3. An image-taking apparatus as defined in claim 2 further comprising a linkage which links the filter holder means with the movable member so that the filter holder means is moved away from the taking lens system in response to movement of the movable member away from the taking lens system.

4. An image-taking apparatus as defined in claim 1 further comprising a linkage which links the filter holder means with the movable member so that the filter holder means is moved away from the taking lens system in response to movement of the movable member away from the taking lens system.

5. The apparatus of claim 1, wherein the urging means places the filter in contact with the taking lens for a predetermined range of movement of the taking lens.

6. The apparatus of claim 1, wherein the filter is not in contact with the taking lens system when the movable member is moved away beyond a predetermined distance from the taking lens system.

7. The apparatus of claim 1, wherein the taking lens system is mounted on a frame mount that is separate from that of the filter holder with the movable member.

8. An image-taking apparatus comprising:
a taking lens system;
a filter holder which holds a filter to be brought into contact with the taking lens system;
a movable member which moves in the direction of the optical axis of the taking lens system;
a moving mechanism for moving the movable member; and
an urging device which is disposed between the filter holder and the movable member and urges the filter holder toward the taking lens system in the direction of the optical axis thereof.

9. The image-taking apparatus of claim 8, wherein the filter holder comprises a holding portion which holds a plurality of filters, and a support portion which movably supports the holding portion so that each of the filters held by the holding portion can be positioned on the optical axis of the taking lens system.

10. The image-taking apparatus of claim 9 further comprising:
a linkage which links the filter holder with the movable member such that the filter holder is moved away from the taking lens system in response to movement of the movable member away from the taking lens system.

11. The image-taking apparatus of claim 8 further comprising:
a linkage which links the filter holder with the movable member such that the filter holder means is moved away from the taking lens system in response to movement of the movable member away from the taking lens system.

12. The image-taking apparatus of claim 8, wherein the urging device places the filter in contact with the taking lens for a predetermined range of movement of the taking lens.

13. The image-taking apparatus of claim 8, wherein the filter is not in contact with the taking lens system when the movable member is moved away beyond a predetermined distance from the taking lens system.

14. The image-taking apparatus of claim 8, wherein the taking lens system is mounted on a frame mount that is separate from that of the filter holder with the movable member.

* * * * *